(12) United States Patent
Heikkilä et al.

(10) Patent No.: US 10,473,594 B2
(45) Date of Patent: Nov. 12, 2019

(54) ARRANGEMENT, METHOD, APPARATUS AND SOFTWARE FOR INSPECTING A CONTAINER

(71) Applicant: Conexbird Oy, Palokka (FI)

(72) Inventors: Teuvo Heikkilä, Palokka (FI); Janne Juhala, Jyväskylä (FI)

(73) Assignee: CONEXBIRD OY, Palokka (FI)

( * ) Notice: Subject to any disclaimer, the term of this patent is extended or adjusted under 35 U.S.C. 154(b) by 240 days.

(21) Appl. No.: 15/557,160

(22) PCT Filed: Mar. 11, 2016

(86) PCT No.: PCT/FI2016/050154
§ 371 (c)(1),
(2) Date: Sep. 11, 2017

(87) PCT Pub. No.: WO2016/146887
PCT Pub. Date: Sep. 22, 2016

(65) Prior Publication Data
US 2018/0038805 A1    Feb. 8, 2018

(30) Foreign Application Priority Data

Mar. 13, 2015 (FI) ..................................... 20155171

(51) Int. Cl.
*G06K 9/00* (2006.01)
*G01N 21/90* (2006.01)
(Continued)

(52) U.S. Cl.
CPC ......... *G01N 21/9072* (2013.01); *G01B 11/30* (2013.01); *G01C 11/06* (2013.01);
(Continued)

(58) Field of Classification Search
CPC ...... G06F 3/011; G06F 3/0304; G06F 3/0346; G06F 16/2264; G06F 16/9024;
(Continued)

(56) References Cited

U.S. PATENT DOCUMENTS 7,822,273 B1    10/2010  Arcaini et al.
2005/0151841 A1   7/2005  Nelson et al.
(Continued)

FOREIGN PATENT DOCUMENTS

JP    2006220543 A    8/2006
JP    2007322173 A    12/2007
(Continued)

OTHER PUBLICATIONS

International Search Report, Application No. PCT/FI2016/050154, dated Jun. 10, 2016, 7 pages.
(Continued)

*Primary Examiner* — Duy M Dang
(74) *Attorney, Agent, or Firm* — Ziegler IP Law Group, LLC

(57) ABSTRACT

An arrangement for inspecting a container and a method for inspecting a container. The arrangement is also directed to software and a device for carrying out the inspecting wherein the method for inspecting includes receiving image data on a container, verifying the location and/or position data of the image data in relation to the container, analyzing the received image data, and detecting possible damage points.

20 Claims, 10 Drawing Sheets

(51) Int. Cl.
*G01B 11/30* (2006.01)
*G06Q 10/08* (2012.01)
*G01C 11/06* (2006.01)
*G06T 7/00* (2017.01)
*G06T 7/73* (2017.01)
*G01S 17/06* (2006.01)
*G06T 15/04* (2011.01)
*H04N 5/247* (2006.01)
*G01C 15/00* (2006.01)
*G06Q 50/28* (2012.01)
*G01N 21/95* (2006.01)
*G01N 21/88* (2006.01)

(52) U.S. Cl.
CPC ............ *G01C 15/00* (2013.01); *G01N 21/95* (2013.01); *G01S 17/06* (2013.01); *G06Q 10/08* (2013.01); *G06Q 50/28* (2013.01); *G06T 7/001* (2013.01); *G06T 7/0008* (2013.01); *G06T 7/74* (2017.01); *G06T 7/75* (2017.01); *G06T 15/04* (2013.01); *H04N 5/247* (2013.01); *G01N 2021/8861* (2013.01); *G06Q 10/083* (2013.01); *G06T 2207/10016* (2013.01); *G06T 2207/10024* (2013.01); *G06T 2207/10028* (2013.01); *G06T 2207/20076* (2013.01); *G06T 2207/30244* (2013.01)

(58) Field of Classification Search
CPC ...... A63F 13/213; A63F 13/24; A63F 13/426; A63F 13/428; A63F 13/655; A63F 13/00; G06T 7/73; G06T 2207/30128; G06K 9/00221; G06K 9/00335; G06K 9/00369; G06K 9/00771; G06K 9/6202; G08G 17/00; G08C 17/02; H04N 5/2226; G06N 3/04; G06N 3/08; G06N 7/181; G01N 21/90; G01N 21/8851; G01N 21/88; G01N 21/9081; G01N 21/909; B65D 90/48; G01C 11/00; B23Q 17/2409

USPC ........................................................ 382/141
See application file for complete search history.

(56) References Cited

U.S. PATENT DOCUMENTS

| | | | | |
|---|---|---|---|---|
| 2008/0001104 | A1* | 1/2008 | Voigt | G01N 21/8851 |
| | | | | 382/141 |
| 2008/0100706 | A1* | 5/2008 | Breed | B60C 11/24 |
| | | | | 348/143 |
| 2008/0303897 | A1 | 12/2008 | Twitchell, Jr. | |
| 2008/0310701 | A1* | 12/2008 | Caroli | G01B 11/25 |
| | | | | 382/141 |
| 2009/0108065 | A1 | 4/2009 | King et al. | |
| 2009/0323121 | A1 | 12/2009 | Valkenburg et al. | |
| 2014/0240699 | A1* | 8/2014 | Lindner | B07C 5/3408 |
| | | | | 356/240.1 |
| 2014/0345382 | A1* | 11/2014 | Heikkila | B66C 13/16 |
| | | | | 73/579 |

FOREIGN PATENT DOCUMENTS

| | | |
|---|---|---|
| KR | 20050022068 A | 3/2005 |
| KR | 100701521 B1 | 3/2007 |
| WO | 9827505 A2 | 6/1998 |
| WO | 20071222221 A1 | 11/2007 |
| WO | 2014118391 A2 | 8/2014 |

OTHER PUBLICATIONS

Written Opinion of the International Searching Authority, Application No. PCT/FI2016/050154, dated Jun. 10, 2016, 8 pages.
Search Report of the European Patent Office for European Application No. 16764284.2 dated Jan. 4, 2019, 11 pages.

* cited by examiner

ARRANGEMENT, METHOD, APPARATUS AND SOFTWARE FOR INSPECTING A CONTAINER

FIELD

The aspects of the disclosed embodiments relate to a container inspection arrangement and a method for inspecting a container. The aspects of the disclosed embodiments also relate to software for performing the method steps, and an apparatus for executing the software.

BACKGROUND

Containers are used for transporting goods and cargo. The contents to be transported can be transferred in a container from one means of transport to another, without unloading and reloading the contents. Containers are constantly transported by land, by sea, by rail, and by air. Container logistics is the most common methods for transporting goods or cargo. Worldwide, an estimated 200 million containers are shipped annually, so the quantities are huge.

Containers are normally inspected in special container handling areas. The inspections are related to security, the condition of the container, or its contents. The inspections are carried out to confirm that the container is in good condition, its contents correspond to the cargo data, and the condition of the contents corresponds to the original. Inspections are carried out, among other things, to prevent smuggling or stowing away. Moreover, the containers themselves can be damaged in use.

The condition of the container can be inspected visually. Visual inspection is slow and requires a worker on site. Moreover, a separate inspection area has to be provided, where the worker inspects the interior and the exterior of the container. For carrying out an interior inspection, the container may be opened. An unopened container may be scanned, or its carbon dioxide content can be measured. The contents of the container can be determined by scanning, but the method is expensive. The carbon dioxide content can be measured via the vent holes of the container by separate measuring devices. A handheld carbon dioxide meter is not useful nor efficient for large numbers of containers on large container handling areas. Handheld measuring devices are primarily suitable for targeted inspections. Excess load, weight deviation or a corresponding state of imbalance can be detected by weighing. However, the weighing is not sufficient to find out the cause, that is, whether the result is possibly due to a stowaway, smuggling, a change in the condition of the contents, or a deviation in the contents from that entered in the consignment note.

In container logistics, containers are being damaged all the time. Reports on container damage are given to the owners of the containers. The inspection of an empty container is normally slow. Moreover, it takes time to compile and accept the container inspection results. It is common that the cause of damage and the time period of the incident remain unclear. Thus, the costs for the damage will be borne by the owner of the container, and possible feedback with a repair proposal will not reach the operator that caused the damage.

Container inspection methods increase the turnaround time in container handling areas. Moreover, the container inspection methods require the addition of a process step and/or human resources to container handling.

SUMMARY

It is an aim of the aspects of the disclosed embodiments to speed up the turnaround times of containers to be inspected. It is another aim of the invention to provide a container inspection arrangement that makes container inspections more efficient and more consistent.

In an embodiment, an arrangement for container inspection comprises means for receiving image data on a container, means for verifying the location and/or position data of the image data in relation to the container, means for analyzing the received image data, and means for detecting possible damage points.

In an embodiment, a method for inspecting container comprises receiving image data on a container, identifying the point of container to which the received image data relates, analyzing the received image data, and detecting a possible damage point in the container. In this context, image data on the container or image data taken of the container refers to image data relating to the container or a part of it; an image that contains data on the container.

In an embodiment, the method steps may be carried out by applying software means and/or an apparatus for executing them.

DESCRIPTION OF THE DRAWINGS

In the following, embodiments of the invention will be described in more detail by referring to the appended figures, in which.

DESCRIPTION OF THE EMBODIMENTS

The handling of containers is arranged on specific areas. For example in harbours, dedicated container terminals are provided for the handling of containers. The containers are loaded on board a ship or unloaded by specific container cranes. The containers may be transferred to the harbour stockyard to wait for reshipping, and from there, or alternatively directly, to e.g. trains or trailer trucks for onward transport. At the stage of transshipment, the containers, their condition and contents may be inspected. According to the embodiments, images of a container are taken at the container handling stage. The image data is transferred to software for analysis. On the basis of the analysis, potential damage points may be detected. A three-dimensional object may be formed of the image data, also including the detected potential damage points. For example, an existing 3D model of the container may be supplemented with image data, other received information, and/or information derived from the image data. The formed 3D object may be examined three-dimensionally from different sides. The 3D object to be formed may be produced in an automated or partially automated way, and it may be controlled, supplemented or focused on manually. The analysis, modelling and 3D presentation of the image data enable remote inspection of the object, whereby the inspector does not need to be in the close vicinity of the container at the time of the inspection. This improves the safety at work and the working conditions of the inspecting persons. The modelling also enables simultaneous viewing of the same object from different directions, viewing by different users, comparing, repeating, and reviewing. This makes it possible to reduce, correct or even eliminate inspection errors, to carry out inspections of more consistent quality, and to carry out double inspection, if necessary. The analysis of the image data, as well as the storage, correlating and processing of the received and analyzed data, all in their parts, enable to automate reporting and evaluation. This, in turn, speeds up the overall processing and contributes to the production of results and reports of more consistent quality.

Figure 1:
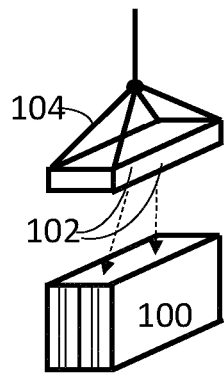
FIG. 1 shows a container inspection arrangement according to an embodiment.

FIG. 1 shows an arrangement for inspecting a container according to an embodiment of the invention. A container 100 is gripped by a gripper element 104 of a container handling apparatus for transferring the container 100. The gripper element 104 is equipped with at least one camera or more cameras 102. The camera 102 is placed in the gripper element 104 in such a way that when the container 100 is gripped by the gripper element 104, the camera 102 is trained on the container 100, being placed in that part of the gripper element 104 that is facing the container 100 to be gripped. The camera 102 placed in the gripper element 104 makes it possible to take images of the top of the container 100, for imaging the top side of the container 100. In this way, data is obtained on the topmost exterior side of the container 100, whose condition is difficult to observe without auxiliary instruments. For example, it may be difficult or time consuming for an inspector to inspect the condition of the exterior top side of the container 100. By means of cameras 102 according to the embodiment, the images for the inspection are obtained already at the initial lifting stage when the gripper element 104 is approaching the container 100.

Figure 2:
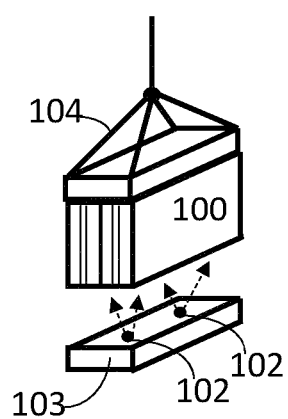
FIG. 2 shows a container inspection arrangement according to an embodiment.

In FIG. 2, the container 100 is being transferred by the container handling apparatus. The container 100 has been lifted up in the air by the gripper element 104 of the container handling apparatus, and the container 100 is intended to be lowered down on a container measuring platform 103. In the embodiment of FIG. 2, the frame of the container measuring platform 103 is equipped with one or more cameras 102. The camera 102 arranged in the container measuring platform 103 makes it possible to take images of the bottom of the container 100, for imaging the bottom side of the container 100. In this way, data on the lowermost exterior side of the container 100 is obtained. Without the camera placement according to the embodiments, inspecting the lower exterior side of the container 100 would require lifting of the container 100. Visual inspection under the container is not safe. Viewing the exterior bottom side of the container 100 may be difficult or time consuming. By means of the camera 102 according to the embodiment, images for the inspection are obtained at the stage of transferring, upon lowering down the container 100 when the container 100 to be lowered down is approaching the container measuring platform 103. According to the embodiment, the container 100 does not need to be separately lifted for inspecting the lower side of the container 100, or its condition.

Figure 3:
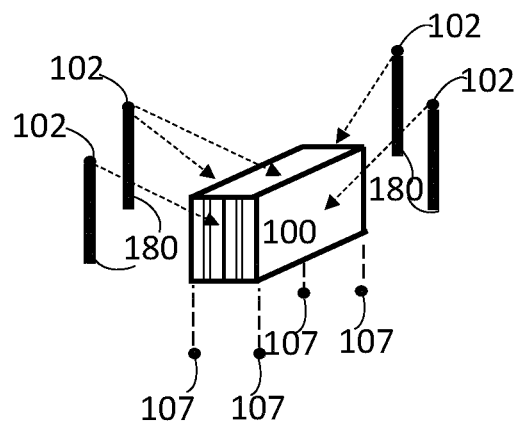
FIG. 3 shows a container inspection arrangement according to an embodiment.
Figure 4:
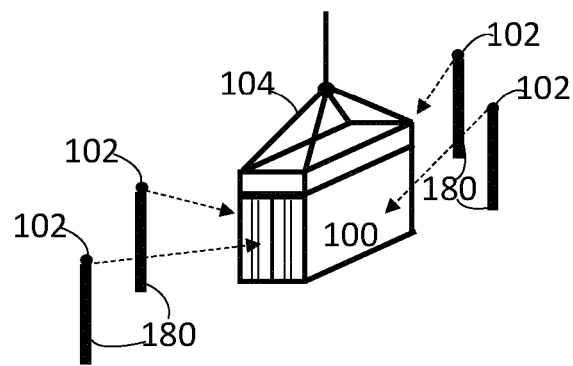
FIG. 4 shows a container inspection arrangement according to an embodiment.

FIG. 3 shows an arrangement for container inspection according to an embodiment of the invention. In FIG. 3, one or more cameras 102 are installed in masts 180 in a container handling area. FIG. 3 also shows a ranging device 107. The ranging device 107 may be placed, for example, in a container measuring area, and its/their position in relation to the camera 102 or the camera mast 180 is known. The ranging device 107 may be used to give the operator of the container handling apparatus an indication of the direction and the position, where the container 100 should be transferred in order to be successfully imaged and/or measured by means of the camera 102. The masts 180 may be placed around the periphery of the container handling area, for example in such a way that one mast 180 with a camera 102 is placed on each side of the container 100. The masts may be placed at the corners of the container 100 to be lowered down, as shown in FIG. 4. In FIG. 3, the container 100 is lowered in its place in the container handling area as indicated by data from the ranging devices 107. The side walls and the topmost wall of the exterior walls of the container 100 may be imaged by cameras 102 in the masts 180. In the embodiment of FIG. 4, the cameras 102 placed in the masts 180 image the container 100, or parts of it, when the container 100 is being transferred. In the embodiment of FIG. 4, when imaging the container 100 to be lowered down on the platform or lifted up from it, it is possible to take an image of a part of the container wall at one moment of time, and a corresponding image of an adjacent part of the container wall at the next moment of time. In this way, it is possible to obtain several shots of the wall and possibly a more accurate result for viewing by means of several images. The camera 102 may be focused and zoomed in on a specific point while the container 100 is moving. Different parts of the container 100 to be imaged are zoomed in by the camera at different moments of time.

Figure 5A:
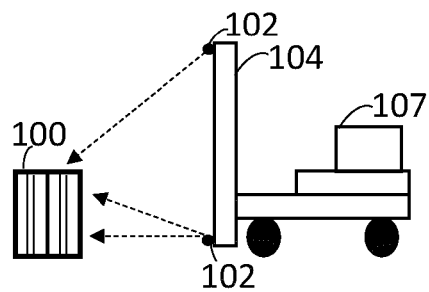
FIGS. 5*abc* show a container inspection arrangement according to an embodiment.
Figure 5B:
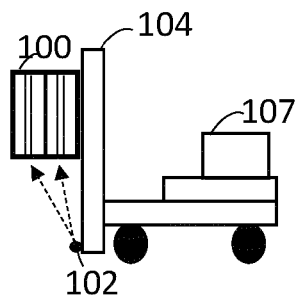
Figure 5C:
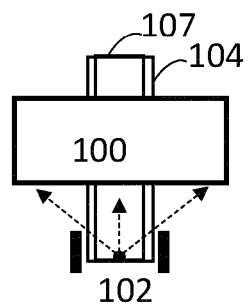

FIGS. 5abc show a container inspection arrangement according to an embodiment. The gripper element 104 is movable and approaches the container 100. The ranging device 107 provides information about the distance between the gripper element 104 and the container 100. By means of the ranging data 107, the gripper element 104 may be guided to the vicinity of the container 100 in a controlled manner so that the gripper element 104 is in its correct position with respect to the container 100, to enable gripping and transferring. The gripper element is equipped with at least one camera or more cameras 102. FIG. 5a is a side view showing the gripper element 104 approaching the container 100. When approaching the container 100, the camera 102 may image the front side and the top side of the container 100, as shown by broken lines in FIG. 5a. FIG. 5b is a side view showing the container 100 lifted up in the air by the gripper element 104. The gripper element 104 may comprise forks similar to a forklift, for lifting the container 100. The gripper element 104 may comprise means for gripping the container, for example clamp-like parts for gripping and lifting the container. When the container 100 is in the air, as shown in FIG. 5b, the camera 102 placed in the gripper element 104 may be used to image the bottom side of the container 100. FIG. 5c shows the container 100 lifted up by the gripper element 104, and the camera 102 imaging the bottom side of the container 100, in a rear view from the direction of the container 100. In the embodiments of FIGS. 5abc, the container 100 is imaged by the camera 102 when the container 100 is being transferred, at the same time and/or as a part of the container transfer step. In this way, information about the container 100 is obtained without separate steps. Viewing the container according to the embodiments does not require manual inspection by any person at said moment of time, nor pauses for transferring the container or the presence of any person in the container inspection area.

Figure 6:
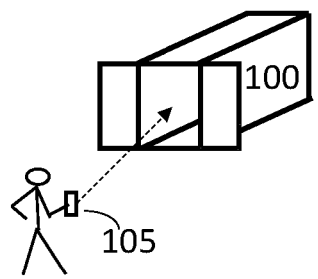
FIG. 6 shows a container inspection arrangement according to an embodiment.

FIG. 6 shows an arrangement for container inspection according to an embodiment. In the embodiment of FIG. 6, the camera for imaging the container 100 is integrated in a user terminal 105. Instead of or in addition to visual inspection by a user, the user may image the container 100 or parts of it by the camera in the terminal 105. The user terminal 105 may be used e.g. for supplementing the images taken by the cameras in the container handling apparatus outside the container. In addition to the exterior sides, the user terminal 105 is suitable for imaging the interior parts of the container, as shown in FIG. 6 in which the container 100 is open and the camera in the terminal 105 shoots the inside of the container 100. A given focus or image point may be provided inside the container 100, on which the camera of the terminal 105 is trained for taking an image. For example, the camera 105 may be trained on the interior rear wall of the container, or the corner between the rear wall and the side wall, or in such a way that a corner between the rear wall and two side walls is on the edge of the image area. The images are typically taken in a predetermined way, from a given distance, with determined camera settings, from determined locations. Thus, images taken of corresponding points of containers are obtained, which images correspond to each other. The terminal 105 may also be used to produce more detailed image information on desired points of the container. For example, a specific point of the container may be imaged in more detail on the basis of a visual observation.

Figure 7:
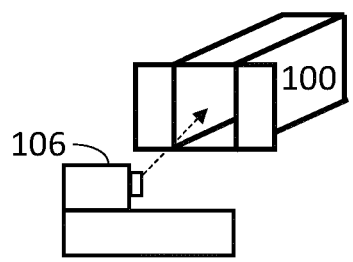
FIG. 7 shows a container inspection arrangement according to an embodiment.

FIG. 7 shows an arrangement for container inspection according to an embodiment. In the embodiment of FIG. 7, the container 100 is imaged by means of an imaging robot 106. The imaging robot 106 may be remote-controlled, in which case a remote user selects the points to be imaged and the settings. The imaging robot 106 may be programmed to take specific pictures of a container 100 placed in a specific location, for example on the basis of selected coordinates. The imaging robot 106 may obtain information from a ranging device, whereby the imaging robot 106 has access to data about the distance between it and the container 100 in addition to the image data. A given distance from the container 100 and an object detected in the image may induce triggering of the camera and shooting a picture of the object. The camera placed in the container handling apparatus may be an imaging robot. Thus, for example a given path, function or location of the container handling apparatus, or a part of it, may induce triggering of the camera and shooting. Data on the images taken or on the objects on which the camera is trained may be transmitted to a software unit. The camera unit, the camera robot or the camera device may comprise a programming unit with a pattern recognition algorithm and means for executing it. Pattern recognition may be applied to detect certain features or objects which should be imaged in more detail. For example, a detected point of discontinuity or suspected defect may be imaged in more detail for closer viewing.

Figure 8:
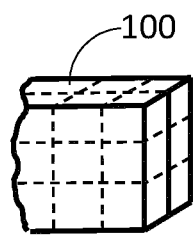
FIG. 8 shows a container inspection arrangement according to an embodiment.

FIG. 8 shows a container inspection arrangement according to an embodiment. In the embodiment of FIG. 8, rays of light are reflected onto the surface of the container 100, shown by broken lines in FIG. 8. Instead of rays, light may be reflected in spots on the surface of the container 100. The light to be reflected may be laser light or other coherent or suitable light. If there is damage or a discontinuity on the surface of the container 100, the light reflected from it will be different from light reflected from the surface of an intact container which may be straight and continuous. In this way, reflecting light onto the surface of the container 100 will contribute to the detecting of damage automatically by means of analysis software as well as visually by the human eye. The reflecting of the light may be monitored visually and/or by software, for example by means of image data, an analysis method and/or a pattern recognition method.

In the embodiments, the container handling apparatus or the container handling area is equipped with a camera for obtaining image data on the container. The container handling apparatus may comprise a crane, a straddle carrier, a reach stacker, a measuring platform, a measuring device, or the like. Imaging according to the embodiments may be performed during storage or transfer of the container, such as during loading or unloading. In the embodiments, the triggering of at least one camera may be automated. For example, a motion sensor may induce triggering of the camera, either upon detecting a movement or at the end of the movement. The image may be taken in response to data transmitted by at least one ranging device. For example, a container detected in a given location may be imaged. The camera may be triggered in response to detecting a given container identification. The container identification may be detected from received image data, or it may be received together with or in addition to images, for example entered by a user. The imaging function may be triggered by a confirmation from pattern recognition that the container is, at a given accuracy, in the correct alignment and in the correct position, in a predetermined location. The camera(s) may be triggered by a voice command. A given movement or gesture, either by the user or, for example, the container handling apparatus or a part of it, may induce triggering of the camera and shooting of an image. In addition or as an alternative, the cameras may be remote controlled so that software remote from the camera will display the image taken by the camera, and based on displayed image shooting time may be determined manually to trigger one or more cameras.

The cameras may move and take a given number of images in a given time. The images may show the object, such as the container or its wall, in an overlapping manner so that the same part of the container is shown in a number of images. A given point may be zoomed in. Using several images and/or imaging from a close distance, the pixel accuracy is better. In this way, it is possible to obtain more accurate, more detailed information about the object. For example, the interior of the container comprises a lot of data in the depth direction, or a wall requires a relatively large shooting angle, if it is represented in a single image. By means of several images, more detailed images may be obtained, focused on part of a larger surface or entity. By combining successive images taken of adjacent locations, more detailed information of the object is obtained than by a single wide-angle image.

In the embodiments, the images may be used to detect mechanical defects, paint defects, graffito, surface detects, structural defects, dirtiness, holes, depressions, bucklings, corrosion, beam defects, bends, and corresponding defects of the container detectable from the image data. Similar defects may also be inspected for the content of the container. The images may be used to inspect, for example, warping, cleanness, straightness, colour differences. Various imaging techniques may be utilized and/or combined to analyze and investigate different features. By analyzing image data, it is possible to detect information that is not even discernible to the human eye. It is thus possible to repair weak points before they become visible damage.

The images may be composed of still camera images, for example one image showing one wall of the container, or successive images taken of adjacent parts of an entire wall of the container, the container and the camera moving in relation to each other. The images may be video images; that is, the object is recorded on video for a given period of time. The cameras may be pointed to a given direction and be stationary while the object is moving. The cameras may move and turn, whereby different parts of the image may be imaged by the same camera, and/or the camera may follow a moving object, and/or the camera may be focused on a desired point of the object to be imaged. For example, in a focused camera view, the vertical edge of the container may be recognized and used for focusing the camera for taking an image, for example at a given distance from the vertical edge. In the camera view, a corner may be recognized, on the basis of which the camera may shoot the adjacent wall or several walls. The image view may be processed by applying various algorithms, for example pattern recognition. The data on the location and/or position of the images taken may be attached to the image data, for example in its metafile, and transmitted with the image data. The algorithms processing the image view may recognize certain features, for example by comparing them with predetermined limit values. The limit values may relate to, for example, the location, geometry or surface structure of the container.

The containers are identified on the basis of e.g. the freight declaration, preliminary data, a container identification, or the like. The container identification on the wall of the container may be imaged, and the container and its type may be identified by means of said image data. The container identification may be retrieved, input or otherwise associated with the data of the image to be taken of the container. The data available on the container, such as possible freight declaration, log data, owner data, location data, etc, may be associated with the reports, listings and/or an object to be formed from the image data. On the basis of this data, the container may be identified, and default and/or limit values may be searched for it, for comparing them with the image view and/or data.

In some embodiments, the imaging relating to the container inspection does not require the presence of a worker. In these embodiments, the imaging may be fully automated, without a user, or remote controlled, the user being remote from the imaging location. This improves safety at work and reduces the risk of accidents during container inspections, as workers do not need to be amidst large, heavy containers in inspection locations where the containers are being transferred and handled. It is also possible to carry out an automatic preliminary inspection of a container, and to carry out an additional manual inspection if damage is detected. In this way, the number of containers requiring manual inspection may be reduced to a fraction of the number of containers to be inspected.

In an embodiment, a container carried by a truck is driven through a gate to a container handling area. Cameras are placed at the gate so that when the truck is driven through the gate, images of the top, the long sides and possibly the doors of the end wall of the container are taken. If damage in the container is detected at this stage when the truck arrives at the container handling area via the gate, the container may be directly forwarded to closer inspection and/or stored to wait for rejection, acceptance or measures of a repair report. In this way, an indication of possible damage of the container, or a condition that requires further measures, is obtained at an early stage as part of receiving the container, without separate investigations. Any containers arriving at the container handling area, including containers arriving via another way, may be subjected to a corresponding inspection. The container may be imaged, for example, upon unloading and/or loading a ship when the container is lifted by a harbour crane. The cameras may be fastened to the structures of the crane. In connection with the transfer operation, a preliminary inspection may be made, on the basis of which the containers that require further inspection may be transferred directly to a location for carrying out the further inspection. At this stage, the container does not need to be especially lifted off the means of transport. In this way, time, money and resources are saved when one expensive step of lifting the container may be eliminated and the container may be forwarded directly to further inspection. If no fault, damage or other cause for further measures or inspections are found, the container is forwarded to, for example, the step of storage, loading or unloading. The truck is driven to a place for unloading, where cameras may be provided as presented in the above embodiments in connection with FIGS. 1 to 8. When the container is lifted off the load bed of the truck upon unloading, the cameras also image the bottom of the container, as well as the end walls. Images of the side wall and the top may also be obtained at this stage, in addition, or alternatively, to those taken at the gate. In this way, images of all the six sides of the container have been taken by the time it has arrived in the container handling area and been lifted off the truck.

According to the embodiments, the image data is transmitted for analysis and for detecting possible damage. On the basis of the image data and its location and/or position data, the program will identify the point of the container, which the image data relates to. The received image data is analyzed by software. The analysis may be implemented in a variety of ways. The received image data may be analyzed on the basis of, for example, numerical data formed from the image data. The image data consists of pixels consisting of colour values. Software may be applied to process colour data, pixel data, geometric data, etc. For example, the analysis software may detect how many pixels of the wall are black and how many are grey. These may be compared with a predetermined limit value. The analysis software may also return information on the number of pixels whose colour or value could not be determined. In addition or alternatively, the analysis software may search for a predetermined colour of rust, or a colour close to it, from the part of container being inspected. Typically, the long wall of the container is uniformly coloured. Detected colour deviations may indicate damage, a need for further inspection, dirtiness, graffiti, or other extra colour on the wall of the container. The analysis software may also recognize patterns, for example a wall of corrugated profile. If there is a point of discontinuity in the wall, for example if a point of discontinuity is detected in a vertical line in two-dimensional data examined, an indication of this is given in response.

In an embodiment, for analyzing the received image data, the memory unit may be equipped with a presentation of an intact reference container, with which the received image data may be compared. The presentation or model of the reference container may be a graphic, geometrical and/or an image presentation, for example a three-dimensional object. Presentations of different container types may be provided, so that a container of a given type is compared with a reference container of corresponding type. When the location and/or position data of the received image data is known, the corresponding location in the reference container may be compared with it. The difference detected between them may reveal certain points of discontinuation or aspects to be reviewed. If a difference is found between the image of the exterior wall and the reference container, the corresponding location in the interior wall may be reviewed as well. In this way, it is possible to find out if the damage is found on one side of the wall only or on both sides of the wall, being for example a hole or a dent. For specifying the point of damage, it is also possible to review, for example, the adjacent wall or corner, or image data relating to said damaged wall and taken from another direction. In this way, further information on the damage may be obtained.

In an embodiment, a large number of reference images are stored in a storage unit, to be accessible to the running software. There may be hundreds or thousands of reference images, or even more. Reference images may be collected, for example, from received image data on containers, and/or they may be entered separately. There are reference images on intact containers and their different parts, as well as on damaged containers and their different parts. For each reference image, it is known which of them shows an acceptable container and which does not. The reference images may be classified into acceptable and unacceptable ones by the user or by software, for example on the basis of pattern recognition and/or analysis. A default defect code may be associated with a reference image showing a container that is broken, damaged or requires further inspection. On the basis of the reference image, the defect may be, for example, a surface defect, a hole, a mechanical defect, dirt, rust, or bend. The received image data may be compared with reference images, from which the reference image closest to the received image data may be retrieved. The condition of the imaged location of the container is indicated on the basis of this. The received image data may be compared with an average of reference images, for a given feature. The average may be used, for example, as a component for calculation of probability. From the received image data, it is also possible to analyze whether it approaches an image defined to be unacceptable. A relatively large number of reference images enables a reliable analysis based on them. As the number of images increases, various defects and/or discontinuities analyzed may be represented in a reliable way.

From the received image data, it is also possible to collect history data to be used by the analysis software. From the history data it is possible to derive e.g. statistical data on certain types of defects or the occurrence of various defects together, or on the correlation of defects with each other. History data and/or data derived from it may be used as a component in calculating probabilities. If artificial intelligence is utilized, it may take into account the history data and learn from the received image data.

The 3D object formed may be stored in the storage unit of the software unit 901, or uploaded to a cloud storage 903, for example a database 902. The stored images 1020 and the 3D object formed with aid of them are available and retrievable from the storage. The 3D object formed may be displayed as a 3D representation to be viewed by the user.

After the received image data has been analyzed, a 3D object may be formed of it. The storage unit of the apparatus may have a 3D model of the container, for example a graphical representation or a model depicting the geometry of the container. The received image data is added to the surface of the 3D model, for example as texture, in the location of the 3D object indicated by the image data. The software unit 901 may comprise an image processing unit for processing the received image data 1020, identifying the location of said image data in the 3D model, and attaching it to the correct location in the 3D model. In this way, a 3D object is formed which corresponds to the imaged object (container). Furthermore, the 3D object is supplemented with the indication of damage detected on the basis of the image analysis. The corresponding data may be presented in a written report and/or list. The location of the damage is displayed in the 3D object, and it may be visible on two sides of the 3D object, in the same location of the wall. The 3D object includes image data on the container and the results of the analysis on possible damage and other aspects analyzed. The 3D object may be displayed to the user who may examine the object three-dimensionally, rotate it and zoom it in and out. Furthermore, the user may be shown a specific part of the object seen from different angles or directions, next to each other.

Detected damage may be associated with information on the damage, indicating the type of the damage. The damage data is associated with the image data, and it may be reported, listed and displayed in a 3D object. In an embodiment, the storage also contains repair cards which may be automatically retrieved and associated with the damage data. A repair card may contain a repair proposal, a cost estimate, a time estimate, a suggestion for the repairer, and/or a list of spare parts for the repair. On the basis of the repair card, the next measures are known and the containers may be classified and/or handled according to the need for repair. At any stage, the user may modify the 3D object, the report, the list, the damage data, or the repair card. Correcting any data will update the other data, cards, and/or views relating to the same container in a corresponding way. The condition of the container may be reviewed by means of the reports and 3D objects formed by software. The results may be obtained in a fully automated way, without user entries. The user may also control e.g. the cameras either remotely or on site, at the location of the container inspection. The formed reports and views may be reviewed and modified on the display. The owner of the container will see and may verify the detected data as well.

Figure 9:
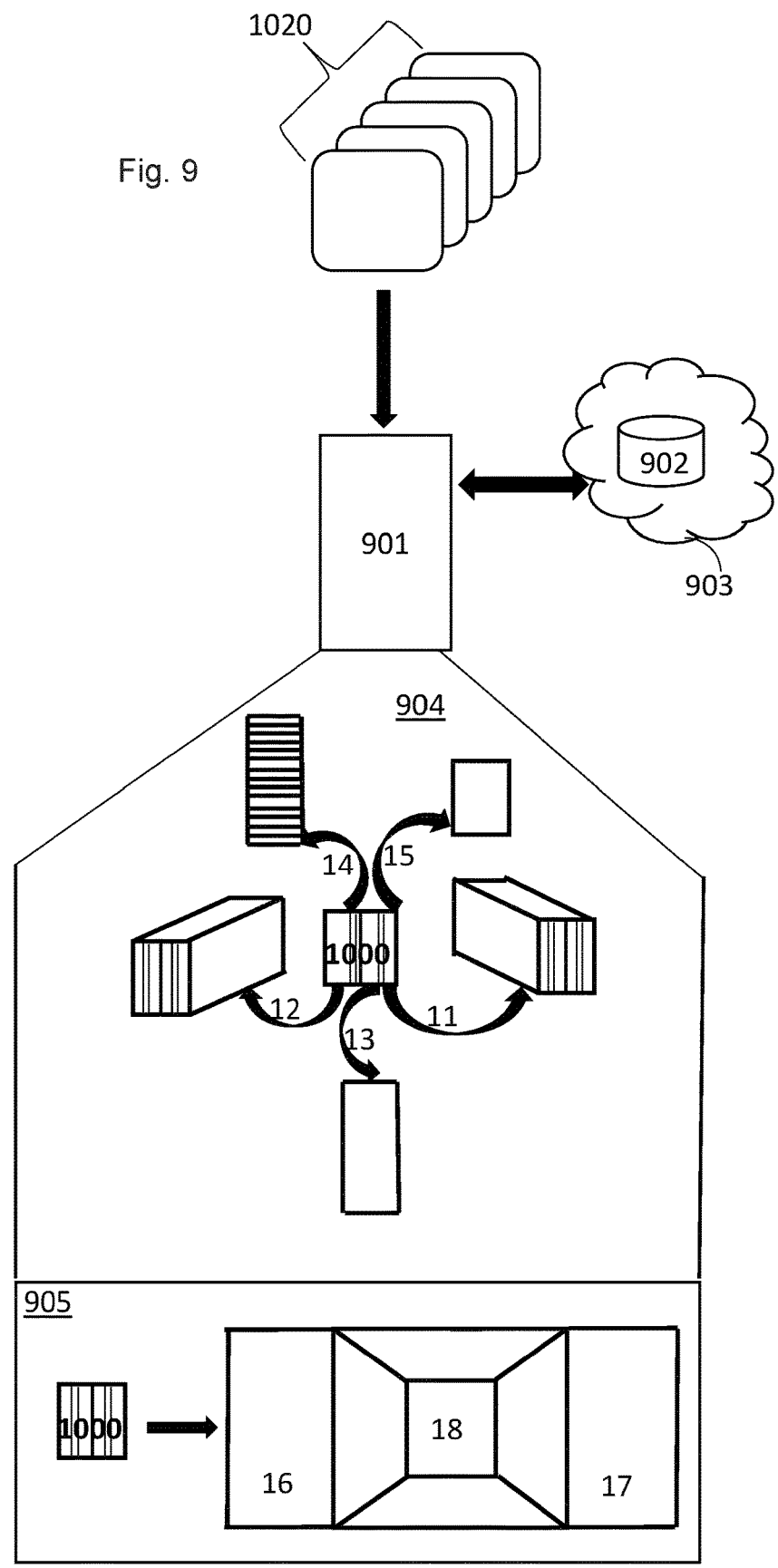
FIG. 9 shows a container inspection arrangement according to an embodiment.

FIG. 9 shows an apparatus for data processing according to an embodiment. Image data 1020 according to at least one or more of the above embodiments is received in the data processing apparatus. The data processing apparatus comprises a software unit 901 for processing and analyzing image data. The received image data 1020 may be stored in the memory of the software unit 901, in a cloud storage 903, or in a database 902, for example. The image data 1020 may contain one or more images or image objects representing different sides of the container, the upper and lower wall, possible also the inside of the container, one or more interior walls of the container, and/or the contents of the container. The software unit 901 receives location and/or position data on the image or image object, entered by the user or provided by e.g. the location sensors of the devices or a ranging device. In addition or alternatively, the location and/or position data of the image object may be verified from the received image data, for example, by means of a pattern recognition algorithm. The location and/or position data may comprise a 2D image or coordinates of the imaged object, the direction of imaging, the width and height of the view of the image. Said location and/or position data may be accessible to the software unit 901 in the form of absolute location data as well as location data with respect to the container. Location and/or position data may be obtained by pattern recognition, for example by identifying the location of the container or a given reference point in the image. The user may enter said additional data in the image data. The imaging device may be placed in a given location, whereby further information may be provided in the image data on the basis of the location and/or settings of the imaging device. The location of the imaging device may be constant, or it may be determined by software and/or manually. The imaging device may be equipped with a sensor (sensors) for determining its location and position. These include, for example, a compass, a gyroscope, an acceleration sensor. By means of this data, the image data relating to one container may be associated with the correct container and the correct location.

The software unit 901 may be placed in the user terminal, in a computer, in a server, in a cloud computer, or in another unit for running the software code.

The user may review a 3D object 1000 formed of the container externally on a display 904. The 3D object 1000 may be rotated on the display 904. For example, the 3D object 1000 may be rotated in the directions indicated by arrows 11, 12 on the display 904 so that the different sides of the container are visible. The lower side of the container may be rotated to a view as indicated by an arrow 13. The top side of the container is shown in a corresponding way by rotating the object 1000 as indicated by an arrow 14. The opposite end flanks are shown in an initial image of the 3D object 1000 and in an image indicated by an arrow 15. If image data for the 3D object has been collected from the interior parts of container as well, the user may examine it by viewing the 3D object 1000 from the inside 905. The doors 16, 17 of the 3D object 1000 of the container may be opened on the display. In this way, the user may look at the interior 18 of the container on the display 905. In addition to the walls, the bottom and the top, the user may also look at the condition of the doors and, for example, the gaskets. The 3D object 1000 of the container also enables zooming in and viewing a desired part of the container in more detail. In other words, the user may zoom in or enlarge the image, focus the view on a desired point, and examine the container virtually. Depending on the quantity and location of received image data, the 3D object to be viewed on the terminal may correspond to the container in full or in part, for example with respect to its exterior walls, if interior images have not been received or included in the object.

The software unit 901 and/or the cloud 903 may comprise an analysis program for processing and/or analyzing image data. Possible damage points may be detected by analyzing and/or by comparing image data or data produced by means of image data. The analysis program may be used to find points of discontinuity or possible damage. In general, the analysis program may be used to produce a result that corresponds to an examination by a user. The analysis program may also detect details that a visual inspection would not reveal yet.

The data and/or 3D object formed may be reviewed on the display. The presented result of the analysis program may be supplemented with an on-site or remote inspection by the user. For example, the user may mark the 3D object with a part that requires inspection, for example on the basis of the age of the container. Moreover, the user may image a certain point of the container by taking a close-up shot on-site, next to the container, or by remote imaging so that a camera focused on the container is triggered by remote control. Said images of the specific point of the container are included in the 3D object and the data attached to it. The images may represent or show, for example, a specific point of the container more closely. The analysis may be repeated by applying the more detailed data. The analysis program may detect a change in the condition of the content of the container, and/or that a value of the container or its content is below or above a set acceptable limit value, and/or a deviation from the cargo data.

In addition to or instead of the image data, the evaluation on the condition may be made by means of data obtained from other measuring. This may include various types of x-ray imaging, surface inspections, ultrasound measurements, scanning, etc. For example, the container may be subjected to measurable vibration. By means of the vibration of the container, it is possible to determine whether the container or the cargo is in the original or acceptable condition. For example, a corroded beam may be detected by vibration measurement, because a corroded beam will vibrate in a way different from a non-corroded one. Said data may be included in the data relating to said container, such as a 3D object, whereby it is presented to the user together with the 3D object and the written report relating to it.

Figure 10:
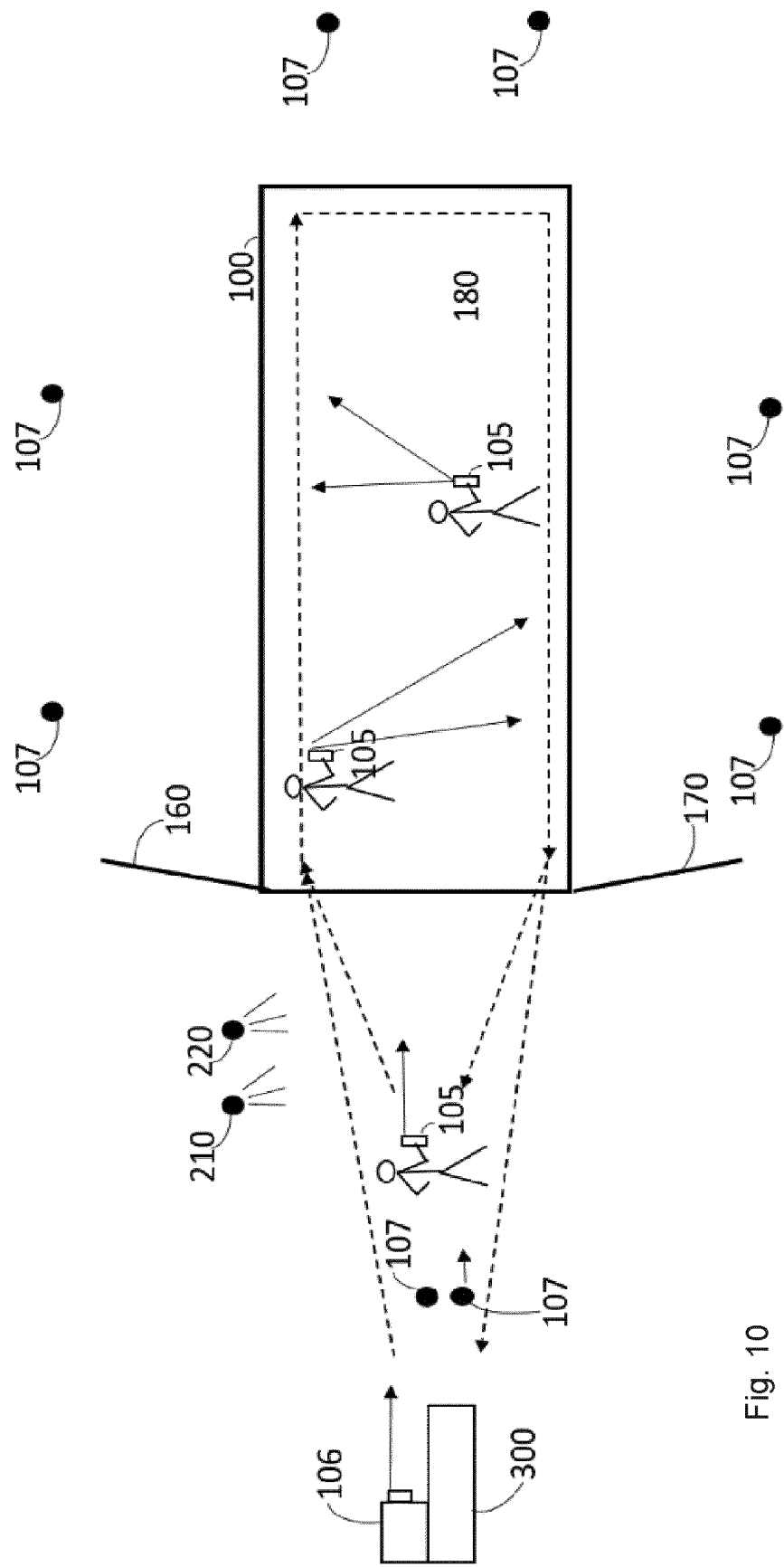
FIG. 10 shows a container inspection arrangement according to an embodiment.

FIG. 10 shows an arrangement for container inspection according to an embodiment. In the embodiment of FIG. 10, the container 100 is guided to its place by means of a ranging device, such as range finders 107. The range finder may be a camera or another sensor capable of detecting distances to objects. Measuring the distance may be based on the emission of electromagnetic radiation and the monitoring of a return signal or an electromagnetic field. The ranging device may be implemented by measuring the travel of light, such as measuring an infra-red or laser beam, or by means of an ultrasound sensor. The ranging may be based on inductive or capacitive measurement.

The camera of the ranging device 107, placed in front of the container, may be used to take images of the interior 180 of the container when the doors 160, 170 have been opened. Images may also be taken by a robot camera 106 in the container handling apparatus 300. Furthermore, images may be taken by the user terminal 105. FIG. 10 shows a Bluetooth antenna 210 and a WLAN antenna 220, by means of which the devices may communicate with each other. For example, the distance data may be transmitted from the range finders 107 to the robot camera 106 or to the user terminal 105. Image data may be transmitted from the camera 106, 105 to image processing software, a server, a computer, a cloud storage, or a corresponding device. The image processing software may also send information on, for example, locations or parts which are of poor quality or missing in the modelling, to the imaging device. The user terminal 105, by which interior parts 180 of the container are imaged in the embodiment of FIG. 10, may be located automatically by means of the range finders 107 and/or Bluetooth antenna 210 and/or WLAN antenna 220, and/or the camera, and/or the image of the camera. For example features present in the interior walls of the container and detectable in the image data may be utilized in the locating. The characteristic features and/or structural data and/or shapes, and/or the identification of the container may be stored in a memory for comparison and/or analysis. The terminal 105 may comprise a compass, an acceleration sensor, a gyroscope, or a corresponding sensor by which the direction or position of the terminal with respect to the ground/the container may be verified. For example by means of a gyroscope, the terminal is provided with information about the position of the terminal with respect to earth gravity (roll, pitch). By means of a compass, information about the direction of imaging with respect to the ground surface is obtained (yawn). The user terminal 105 may guide the user to take images of the interior parts 180 of the container: specific parts, in specific positions, focusing on specific points, etc. The images may be transmitted to image processing software in another device in a wireless manner. Control data may be transmitted from remote software to the imaging robot 106 in a wireless manner. Images taken by the robot 106 in a controlled manner may be transmitted to image processing software in the other device.

Figure 11:
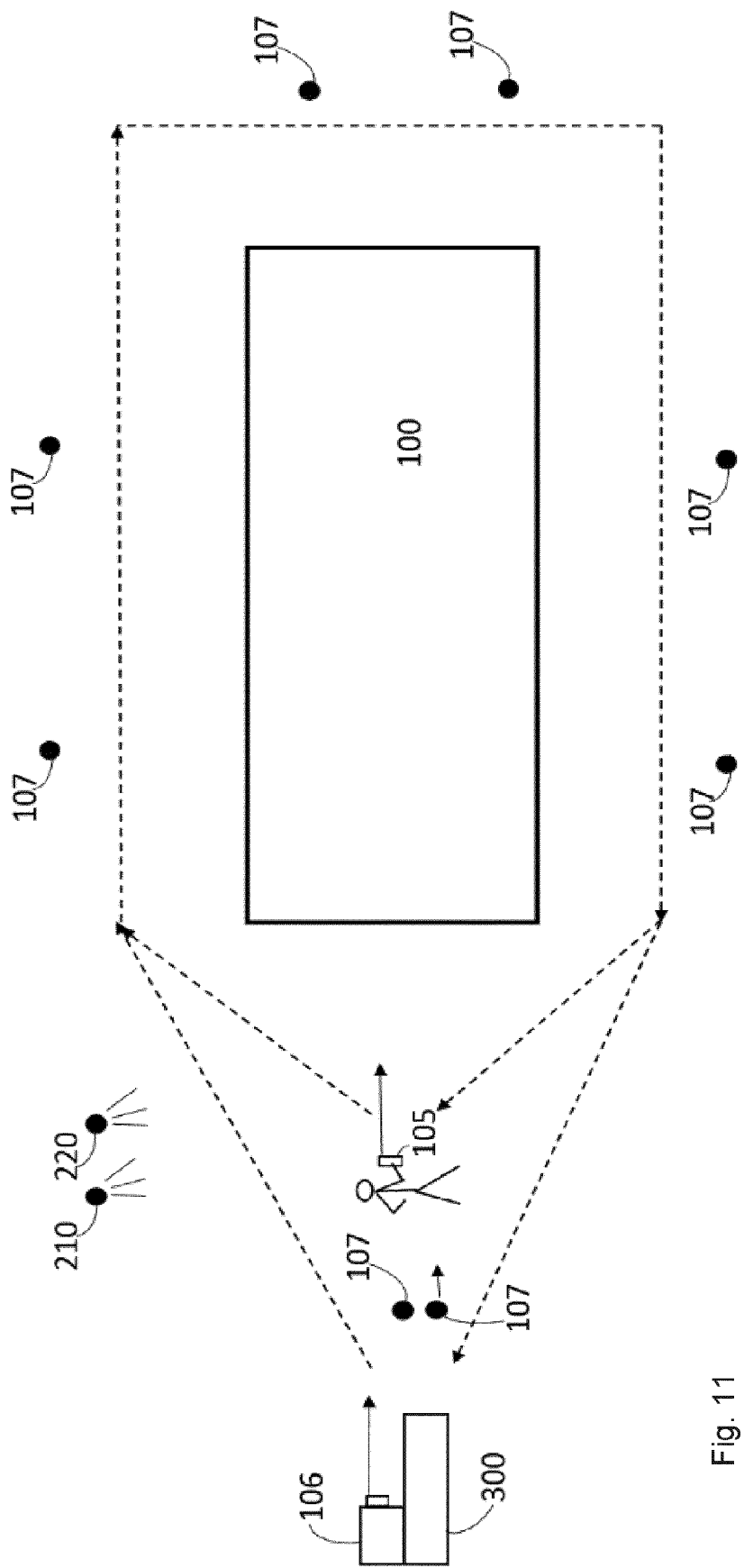
FIG. 11 shows a container inspection arrangement according to an embodiment.

FIG. 11 shows an arrangement for container inspection according to an embodiment. In the embodiment of FIG. 11, the container 100 is examined and imaged from the outside. The imaging may be carried out by a user terminal 105 or by an imaging robot 106. Range finders 107 locate the moving camera 105, 106. Information is transmitted via antennas 210, 220 in a wireless manner, as in the embodiment of FIG. 10. The user's path is shown by broken lines, as in FIG. 10. The user may be guided and the imaging may be controlled by the user via the user interface of the terminal 105. The user interface may be graphic and/or voice controlled, sound producing. According to information transmitted by the range finders 107 to the user terminal 105, the user is instructed to take specific images at specific locations. Furthermore, the user may image a desired part of the container on the basis of visual observations. All the images are transmitted in a wireless manner, for example via the antennas 210, 220, to the image processing software for forming a 3D object. A device for imaging the container 100 from the outside may be located in a way corresponding to the device of FIG. 10 for imaging the interior of the container: by means of range finders 107, antennas 210, 220, an imaging robot 106, image data, the camera of the terminal, or sensors. In the embodiments of FIGS. 10 and 11, the location data of the terminal 105 and the direction data of its camera at the imaging location may be used in a programme controlled way in image processing and/or analysis software. This data may be transmitted with the images, or also to a software unit.

Figure 12:
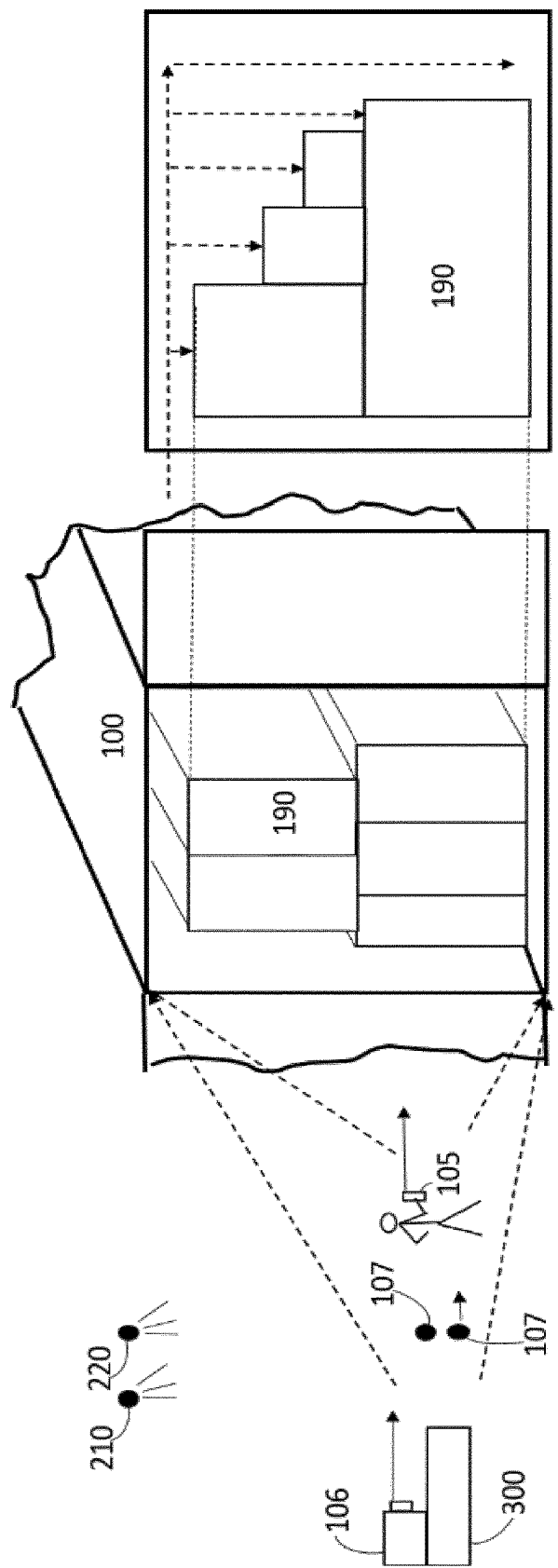
FIG. 12 shows a container inspection arrangement according to an embodiment.

FIG. 12 shows an arrangement for container inspection according to an embodiment. In the embodiment of FIG. 12, the content 190 of the container 100, the cargo, is examined by imaging. Antennas 210, 220 and range finders 107 may be used for locating the terminal 105, as presented in previous. Data may be transmitted in a wireless manner, for example via the antennas 210, 220, as presented in previous. The location and position of the user terminal 105 at each time may be determined, as presented in previous. In FIG. 12, either the imaging robot 106 or the user terminal 105, or both, take images of the content 190 of the container. An example of the imaging path is shown by broken lines in FIG. 12. Several images may be taken of the content 190 of the container, from different viewing angles. By means of these images and possible data on the imaging location and position, the image processing software produces a 3D object of the content 190 of the container for viewing as well.

Figure 13C:
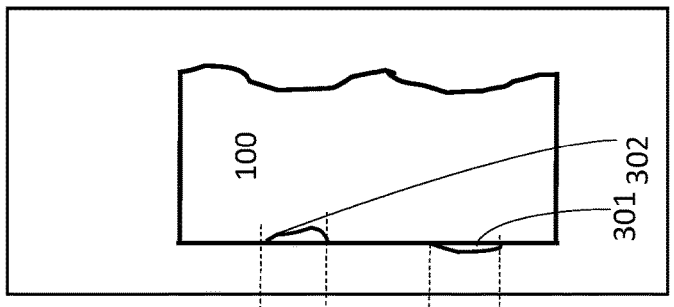
FIGS. 13*abc* shows a three-dimensional model of a container according to an embodiment.
Figure 13B:
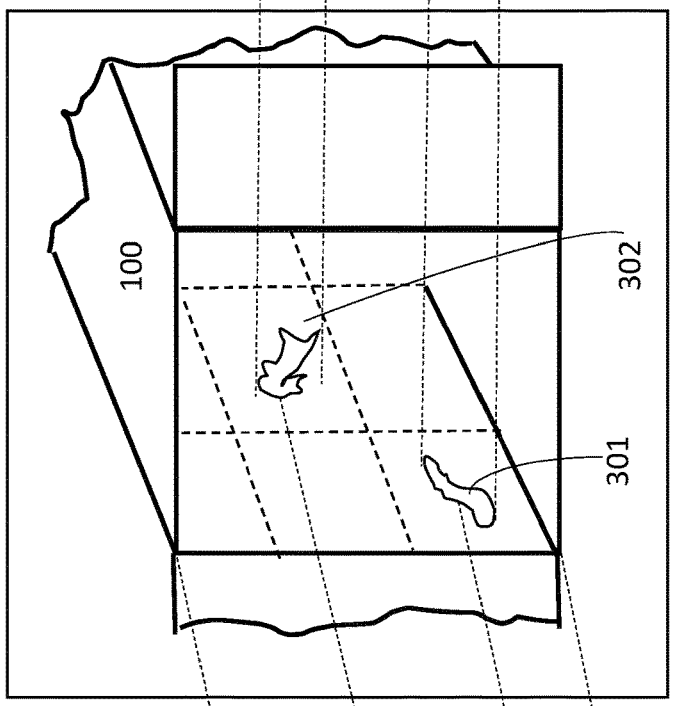
Figure 13A:
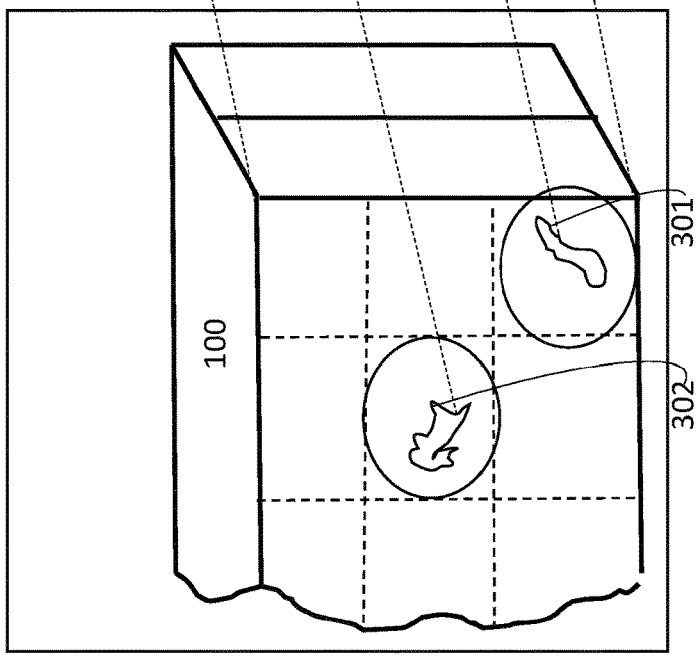

FIGS. 13abc show a 3D model of a container according to an embodiment. The 3D object shown in FIGS. 13abc has been formed on the basis of an existing 3D model, by supplementing it with e.g. image data, analyzed image data and/or other measured or obtained data on the container. The analysis software may compare the data used for forming the 3D object with predetermined limits, calculate straightness values, surfaces and other values, and compare them with default values, apply pattern recognition for finding certain features, locations or damage in the images, or use another suitable method or received data for detecting possible points of discontinuity or other interesting objects. A detected point of discontinuity is shown in a 3D object that is produced by means of received image data. The point of discontinuity is also represented three-dimensionally in the 3D object. In other words, if the point is visible from different directions, it will be represented from different directions by the object as well. The image processing software displays the model to the user. The user may review a desired part of the container quickly by pointing or selecting the part in the 3D object, whereby the system will display all the images in which the selected point is visible. The images may be exterior and/or interior images of the container. The views are seen from different directions and perspectives, whereby the user may quickly review e.g. a potential location of damage from various directions. The user may review the location of damage in adjacent images from different perspectives simultaneously, for example from the outside and the inside of the container. In the image processing, the location of damage may be highlighted for example by colours, by circling or in other ways.

In the embodiment of FIG. 13a, the 3D object of the container shows the container 100 from the outside. In FIG. 13a, two points 301, 302 of discontinuity are shown on the outer surface of the container. The points 301, 302 of discontinuity indicate that there may be a damage, a defect or the like in the structure of the container. The user may examine this on the display by means of the 3D object. In the embodiment of FIG. 13b, the same 3D object is shown from the inside of the container 100. FIG. 13b shows the same points 301, 302 of discontinuity inside the container as were visible on the outside of the container 100. By means of analysis software, potential points 301, 302 of damage have been detected in the same location of the wall, inside and outside. The analysis software has detected that there is no through hole. Thus, the damage is shown on both sides of the wall, as in FIGS. 13ab. The damage may be a buckle or a dent or a bend in the damaged part of the wall. By analyzing the image data, further information on the damage may be derived. As shown in FIG. 13c, the points 301, 302 of damage are also visible when the 3D object is seen from the rear part of the container 100. The points 301, 302 of discontinuity are also visible in the view of FIG. 13c. The points of discontinuity may be, for example, bends in the frame of the container, or buckles in the wall. In FIG. 13c, the exterior surface of the container has bent outward at the damage point 301 and inward in the damage point 302. The convexity/concavity of the bends or buckles are thus visible when the 3D object of the container is viewed from behind. In addition to or instead of detecting damage, pattern recognition and its limit values may be applied to detecting dirtiness of the container and/or the cargo. This may be done in a fully automated way. Containers in need of washing may be forwarded to an appropriate location on a container handling platform for washing. It is also possible that the user indicates a desired part (of the image) for further inspection, for example for (re-)analysis by pattern recognition.

In the user interface, various system views are displayed in addition to the 3D object. Users may be given various rights relating to, for example, access to views, reading and/or modifying them. In a view, it is possible to display not only the formed 3D object but also a list of damage to the container and/or the cargo, a report on the damage, an editable damage list, an approval view, and/or a receiving view. The user may examine both the image view and the written presentation on the damage. The user may add a damage indication to the container data. The user may add a written damage indication in a list, whereby the corresponding data is updated in the image view as well. The user may add a damage indication to an image, for example by using a mouse, whereby the data is updated in the written list of damage as well. The modifications made by the user in one view are automatically updated in the other views and the data relating to said object (container). The user may accept or reject the presented damage indications. The accepted and the rejected damage indications may be differentiated on the display by e.g. colours. Damage data relating to the damage indication, such as the location of the damage, is displayed in the view. On the basis of the damage, the software may retrieve a repair code suitable for the damage from a database, and include it in the data of the damage indication, at least as a proposal. User interface images, objects, system views, and/or links to them may be transmitted to other devices via, for example, email.

The user interface may comprise a touch display, a mouse, a keyboard, a voice controller, etc. In an embodiment, the user interface comprises 3D glasses, with which the user both observes and controls the view of the display. A movement of the head and/or the eyes will generate an input or command for the display. The display may thus be three-dimensional. In an embodiment, the user interface is a virtual glove. Input may be given to the surface of the 3D display or a hologram without an actual display.

In some embodiments, a 3D object and damage reports with repair proposals are automatically generated on the basis of the images of the container. The inspection of the container is thus transferred far away from the container handling area and takes place via the displayed view. Examining the generated view is faster, safer, more reproducible and more efficient than inspecting the containers personally on site. Moreover, damage to containers, reports and other views may be compared, and inspections between containers will be of more consistent quality. The repair proposals or reports may be forwarded directly to the repairing party. Separate work steps or putting down on record will not be needed.

Figure 14:
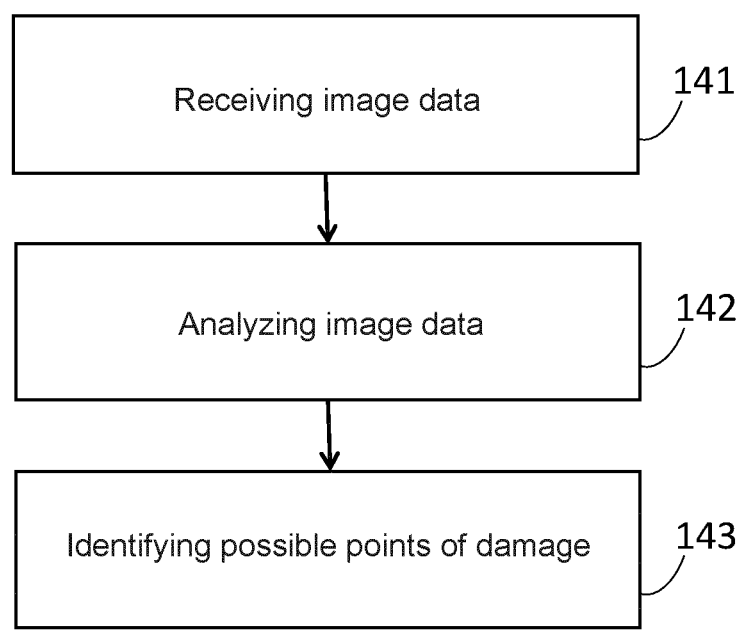
FIG. 14 shows a method for container inspection according to an embodiment.

FIG. 14 shows a method for container inspection according to an embodiment. In the method, image data 141 is received. The image data may be produced by a camera placed in a container handling area. Image data may be produced by at least one camera or more cameras. The camera may be placed in a user terminal, in a container handling apparatus, in a specific fixed location, or be movable within a given area. The image data may contain images of one or more walls of the container, outside and/or inside the container. The received image data may contain image data about at least three walls of the container, advantageously at least four walls, preferably six walls, and/or images of the cargo in the container. The imaging function may be triggered automatically and/or on the basis of a given observation, and/or by remote control. The image data may include light spots and/or segments of light reflected from a light source onto at least one wall of the container.

Location and/or position data relating to the image data is received to accompany or to be attached to the image data. On the basis of it, the image data is associated with the correct container and the correct location in the container. The location and/or position data may be identified from the received image data, for example, by means of a pattern recognition algorithm. The location and position data may relate to a fixed location of the camera, whereby the location data and possible settings and position of the imaging camera determine the angle of viewing. The location and position data may be verified and transmitted with the images or separately on the basis of the location, position and settings of the camera. The location and position data may be entered manually; for example, the user of the terminal may add location and position data to the image data. The camera may also add location and position data to the metadata of the image. The location of the container and/or the movable camera may be determined by means of a ranging device. The location may be determined, for example, in the container handling area.

Received image data is analyzed in step 142. The image data may be analyzed by processing the received data in the form of pixels, numerical data, image data, two-dimensional data, or the like. The analysis software may, for example, examine the geometrical continuity or the occurrence of a given colour or other property. Unidentified or deviating findings may lead to a damage indication or further inspection. The image data may be analyzed by comparing it with an existing model of an intact container. When the location of the image data with respect to the container is known, it may be compared with a corresponding location in a reference container. The comparison will result in finding possible points of damage. The image data may also be compared with a number, such as hundreds or thousands, of images of a container, to find the closest one(s). From a number of reference images, it is also possible to calculate probabilities or averages when analyzing the image data. Moreover, the analysis software may utilize history data and/or artificial intelligence. The software may be learning, whereby it finds damage that has already been detected and the common factors and/or related factors from the newly entered image data faster on the basis of an earlier analysis. The analysis software may also, in response to the detection of a specific type of damage, search for certain features which typically relate to or co-occur with said damage.

Possible damage points of the imaged container are identified 143. The damage points may be identified on the basis of the analysis made. Damage points may also be identified by means of other measurements, and said data may be transmitted to be included in the container data.

The received image data and the detected damage points are placed in the correct locations in the 3D object of the container. The 3D object may be provided with texture on the basis of the image data. By means of the texture, further information on the wall may be obtained. The image data (texture) corresponding to each wall of the model is added to the object, in the location corresponding to the real location. The object may contain information added according to the image data and its location, on one or more walls of the container, interior and/or exterior walls, or relating to the cargo of the container. Potential points of damage detected are also added to the 3D object. The object may be presented in such a way that it may be viewed as a 3D object. The object may be turned and viewed from different directions, from different distances. Several views of a selected point of the object may be displayed simultaneously, from different angles of viewing.

In the method, a report and/or listing and/or a 3D object according to the received image data may be formed by means of the image processing unit. The image data may be analyzed, and a report and/or listing and/or a 3D object may be formed according to the analysis. Features of the image data and/or the 3D object formed may be detected by at least one pattern recognition algorithm. The report and/or listing and/or 3D object containing the corresponding data may be presented in such a way that a change in one of them will produce a corresponding change in other views displaying the corresponding data. The detected damage may be included in the report and/or listing and/or 3D object to be formed. The detected damage may be generated on the basis of input, on the basis of a separate measurement, by analyzing the image data, or in another suitable way. On the basis of the detected damage, a repair card may be associated with said detected damage, containing information relating to the repair of the damage. The repair card may be stored in a memory, or it may be available, for example downloadable. The repair card may be retrieved on the basis of detected damage and associated with the detected damage. Image data, data formed of the images, modified data, and/or associated data may be transmitted between devices in an electronic and/or wireless way.

In an embodiment, a program code and means for running it are provided. The embodiment may comprise a device for running the program code. The device may comprise a memory unit for storing the program code and a processor for running the program code. Upon running, the program code participates in carrying out the following: receiving image data of the container. In connection with or in addition to the image data, location and/or position data of the image data is received. It may be used for determining the location of each image object with respect to the container. The received image data is analyzed. On the basis of the analysis, possible points of damage are detected. Points of damage may also be detected by means of other measurements or be input in the system. The received image data and possible damage indication may be attached to the appropriate point in the 3D object on the basis of the location and/or position data. The image data may form the texture in a 3D model. The texture of the image data may be attached to the surface of the 3D object (container). In this way, a 3D object is formed which includes the 3D model supplemented with the received image data and possible damage indications. The formed 3D object is represented in such a way that it may be viewed in a three-dimensional way. The user may view the formed 3D object from different directions, angles and distances. All the above-mentioned method steps may be implemented by software, by means of software to be run and/or instructions to be carried out.

The invention claimed is:

1. Arrangement for inspecting containers, comprising:
    means for receiving image data taken of a container by a camera, the image data comprising image data of the exterior of the container and of the interior of the container;
    means for verifying the location and/or position data of the image data in relation to the container, and
    means for analyzing the received image data and for detecting possible points of damage, the potential points of damage being configured to be visible at the same point of the wall of the container, inside and outside,
the arrangement being configured to generate a 3D object of the received image data, comprising received image data and a 3D indication of a possible damage point so that in the generated 3D object, the same damage points are visible on the outside of the container and on the inside of the container.

2. The arrangement for inspecting containers according to claim 1, comprising at least one or more cameras are arranged in a container handling area for imaging the container and for generating image data.

3. The arrangement for inspecting containers according to claim 2, wherein at least one or more cameras are placed in a container handling apparatus, in a gripper element of the container handling apparatus, in a platform of the container handling apparatus, in a measuring platform of the container handling apparatus, in a frame element of the container handling apparatus, in a gate of a container handling area, in masts in the container handling area, in a movable imaging robot, or in a mobile terminal.

4. The arrangement for inspecting containers according to claim 1, wherein the image data comprises:
    at least one wall of the container, advantageously at least 3 walls, more advantageously at least 4 walls, preferably 6 walls; and/or
    image data on the cargo in the container.

5. The arrangement for inspecting containers according claim 1, wherein the means for verifying the location and/or position data of the image data in relation to the container comprise at least one of the following:
    a ranging device for determining the location and/or position data of the container, and/or a movable camera for determining the location and/or position data;
    one or more sensors for determining the location and/or position data of the camera and/or of the image data;
    means for entering location and/or position data;
    a pattern recognition program for verifying the location and/or position data in the received image data.

6. The arrangement for inspecting containers according to claim 1, wherein the one or more cameras produce image data automatically and/or on the basis of a given observation and/or by remote control.

7. The arrangement for inspecting containers according to claim 1, further comprising a light source, preferably a laser, for reflecting spots and/or segments of light onto at least one wall of the container to be imaged, and for imaging them together with said wall.

8. The arrangement for inspecting containers according to claim 1 being configured to compile a report and/or a listing of the received image data, containing received image data and an indication of a possible damage point, wherein the report and the listing and the 3D object contain data corresponding to each other, and that the views of them are editable in such a way that a change in one view will cause a corresponding change in the other views representing the corresponding data.

9. The arrangement for inspecting containers according claim 1, comprising at least one pattern recognition algorithm for recognizing features in a focused image taken by the camera, in image data, and/or in a generated 3D object.

10. The arrangement for inspecting containers according to claim 1, wherein the means for detecting possible points of damage comprise at least one of the following:
    analysis software for analyzing image data;
    means for receiving a damage measurement taken by a measuring device, optionally by vibration measurement, and for including it in the data of the container in question.

11. The arrangement for inspecting containers according to claim 1, wherein the means for analyzing the received image data comprise at least one of the following:
    analysis software for analyzing image pixel data;
    analysis software for comparing the received image data with predetermined values;
    analysis software for comparing the received image data with a reference container;
    analysis software for analyzing the received image data by means of reference images; and/or
wherein the means for analyzing the received image data utilize history data and/or artificial intelligence.

12. The arrangement for inspecting containers according to claim 11, wherein on the basis of verified location and/or position data, received image data is included as texture in the surface of the 3D model, and the model also represents the detected damage points in their correct positions in the 3D view of the container.

13. A method for inspecting containers, comprising
receiving image data taken of a container by a camera, the image data comprising image data of the exterior and the interior of the container;
identifying the point of the container to which the received image data relates;
analyzing the received image data, and detecting a possible damage point in the container, the analysis software being used to detect the potential damage points at the same point in the wall of the container, inside and outside; and
generating a 3D object of the received image data, which object contains received image data and an indication of a possible damage point so that the same damage points are visible, in the 3D object, on the outside of the container and on the inside of the container.

14. The method for inspecting containers according to claim 13, wherein the image data comprises at least one of the following:
image data of at least one wall of the container, advantageously at least 3 walls, more advantageously at least 4 walls, preferably 6 walls;
image data of the exterior and the interior of the container, and/or of the cargo in the container;
image data of the container captured automatically and/or on the basis of a specific observation and/or by remote control;
image data of spots and/or segments of light reflected from a light source onto at least one wall of the container.

15. The method for inspecting containers according to claim 13, comprising identifying the point of the container, to which the received image data relates, by one of the following ways:
determining the location and/or position data of the container to be imaged, by means of a ranging device;
determining the location and/or position data of a movable camera by means of a ranging device;
determining the location and/or position data of the camera and/or the image data by one or more sensors;
verifying the location and/or position data from the received image data by pattern recognition software.

16. The method for inspecting containers according to claim 13, comprising compiling a report and/or a listing of the received image data (1020), containing received image data and an indication of a possible damage point, wherein the report and the listing and the 3D object contain corresponding data, and that their views are editable in such a way that a change in one view will generate a corresponding change in the other views representing the corresponding data.

17. The method for inspecting containers according to claim 13, comprising detecting a possible point of damage of the container by at least one of the following:
analyzing received image data,
receiving the result of a measurement made by a measuring device, optionally by vibration measurement, and adding it to the data of said container.

18. The method for inspecting containers according to claim 13, comprising analyzing the received image data by at least one of the following:
analyzing image pixel data by analysis software;
comparing the received image data with predetermined values;
comparing the received image data with corresponding data on a reference container,
analyzing the received image data by reference images.

19. The method for inspecting containers according to claim 13, wherein on the basis of verified location and/or position data, received image data is included as texture in the surface of the 3D model, and the model also shows the detected damage points in their correct positions in the 3D view of the container.

20. An apparatus comprising a memory unit for storing program code and a processor for executing the program code, such that when executing the program code by the processor, the apparatus is arrange to implement the method steps according to the claim 13.

* * * * *